US00PP22501P2

(12) United States Plant Patent
Kordes

(10) Patent No.: US PP22,501 P2
(45) Date of Patent: Feb. 21, 2012

(54) MINIATURE ROSE PLANT NAMED 'KORKIHOT'

(50) Latin Name: *Rosa hybrida*
Varietal Denomination: KORkihot

(75) Inventor: Tim-Hermann Kordes, Klein Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 0 days.

(21) Appl. No.: 12/459,095

(22) Filed: Jun. 25, 2009

(51) Int. Cl.
*A01H 5/00* (2006.01)

(52) U.S. Cl. ..... Plt./121

(58) Field of Classification Search ..... Plt./121
See application file for complete search history.

*Primary Examiner* — Susan B McCormick Ewoldt

(57) ABSTRACT

A new and distinct variety of miniature rose with long lasting, novel hot pink flowers, and dark green and attractive foliage. It exhibits compact, uniform growth and flowering under greenhouse conditions when grown as a potted floral plant. The new variety propagates well from cuttings and by grafting. This new and distinct variety has shown to be uniform and stable in the resulting generations from asexual propagation.

1 Drawing Sheet

SUMMARY OF THE INVENTION

Genus, species and variety denomination: The botanical classification of the new rose plant is *Rosa hybrida,* 'KORkihot'.

CROSS REFERENCES AND FEDERAL R&D STATEMENT

There are no cross-referenced or related applications. This variety was developed without the aid of any research grant.

BACKGROUND OF THE INVENTION

The present discovery constitutes a new and distinct variety of a miniature pot rose plant which was discovered in a cultivated area in September, 2007. Said cultivated area consists of a climate-controlled glass house specially designed for production of potted floral plants, and is owned by the applicant. The new rose variety resulted from a naturally occurring mutation of unknown causation on a branch of 'KORhedani', a patented rose described and illustrated in U.S. Plant Pat. No. 19,598, and issued on Dec. 30, 2008.

The new rose plant was asexually propagated for further evaluation. This new and distinctive miniature rose variety is named 'KORkihot'.

SUMMARY OF THE DISCOVERY

The new rose plant may be distinguished from 'KORhedani', by the following combination of characteristics:

1. 'KORkihot' has hot pink flowers, while the parent plant has dark red flowers.
2. 'KORkihot' has a flower diameter of 40 mm, while the parent plant has a flower diameter of 55 mm.

The new and distinct rose plant was selected due it its':

1. Compact and uniform growth and flowering under greenhouse conditions when grown as a potted floral plant;

2. Abundant, long lasting, and attractive hot pink flowers on upright stems;
3. Resistance to diseases encountered in greenhouse and nursery culture; and
4. Suitability for production from softwood cuttings in floral and nursery containers;

This combination of qualities is not present in prior rose cultivars. These objectives have been substantially achieved and in that distinguish 'KORkihot' from all other varieties of which we are aware.

As part of the rose development program, Tim-Hermann Kordes asexually propagated the mutation by rooting cuttings and conducted evaluations and observations on the resulting plants in a controlled environment in Offenseth-Sparrieshoop, Germany. The resulting seedlings exhibited distinctive physical and biological characteristics. The first asexual reproduction of 'KORkihot' was done by rooting softwood cuttings in October, 2007 at the Rosa-Danica Nursery in Odense, Denmark.

This initial and other subsequent propagations conducted in controlled environments show that the foregoing and all other characteristics of 'KORkihot' come true to form and are transmitted through succeeding generations.

BRIEF DESCRIPTION OF THE DRAWING

The accompanying drawing shows as true as is reasonably possible to obtain in color photographs of this type, the typical characteristics of the buds, flowers, leaves, and stems of 'KORkihot'. Specifically illustrated is: a flower bud, partially opened bloom, open bloom, floral parts, sepals, juvenile foliage, stem exhibiting thorns, and leaves.

DETAILED BOTANICAL DESCRIPTION

The following is a description of 'KORkihot', as observed in its growth in August, 2008 in a nursery in Jackson County, Oreg. on plants of six months of age. Color references are made using The Royal Horticultural Society (London, England) Colour Chart, 2001 except where common terms of color are used.

For a comparison, several physical characteristics of the rose variety 'KORhedani', a rose variety from the same inventor described and illustrated in U.S. Plant Pat. No. 19,598 and issued on Dec. 30, 2008 are compared to 'KORkihot' in Chart 1.

CHART 1

| | 'KORkihot' | 'KORhedani' |
|---|---|---|
| General tonality on open flower | Red-Purple Group N57A | Red Group 53A |
| Flower petal count | 35-40 petals | 30-32 petals |
| Pistil count | Approximately 30-40 | Approximately 60 |

Parent: 'KORhedani'.

Classification:

*Botanical classification.*—*Rosa hybrida*, var. 'KORkihot'.

*Commercial classification.*—Miniature rose.

FLOWER AND FLOWER BUD

Blooming habit: Recurrent.

Flower bud:

*Size.*—Upon opening, 20 mm in length from base of receptacle to end of bud and 12 mm in diameter at its widest point.

*Bud form.*—Long. Pointed ovoid.

*Bud color.*—As sepals first unfold, bud color is Red-Purple Group N66A. When ¼ open, the upper surface of petals is Red-Purple Group N57B, and the lower surface is Red-Purple Group N57B.

*Sepals.*—Size: Average 18-20 mm long×4-5 mm wide. Shape: Sepals generally subulate. Sepal apex is generally cirrose. Strong foliaceous appendages on three of the five sepals. Base is flat at union with receptacle. Quantity: Five. Margins: With stipitate glands. Surface texture: Inner side: Covered in fine white hairs. Outer side: Stipitate glands are present. Color: Upper surface: Green Group 138A. Lower surface: Yellow-Green Group 144A and Yellow-Green Group 144B.

Receptacle:

*Surface.*—Smooth.

*Color.*—Yellow-Green Group 145A.

*Shape.*—Funnel shaped.

*Size.*—6 mm (h)×5 mm (w).

Peduncle:

*Surface.*—With stipitate glands.

*Length.*—30-32 mm average length.

*Diameter.*—1.0-1.5 mm average diameter.

*Color.*—Yellow-Green Group 145A.

*Strength.*—Strong.

*Borne.*—Multiple flower buds per stem, generally 2 to 4.

Flower bloom:

*Fragrance.*—None.

*Duration.*—Long lasting. A blooming plant with flowers has a commercial shelf life of 18 to 20 days. The blooms have a duration on the plant of approximately 14 to 16 days.

*Size.*—Medium for an 8-11 cm pot rose. Average flower diameter is 40 mm when open. Average flower depth is 25 mm.

*Form.*—Shape of flower when viewed from the side: Upon opening, upper part: Convex. Upon opening, lower part: Flat. Open flower, upper part: Flattened convex. Open flower, lower part: Concave.

Color:

*Upon opening, petals.*—Outermost petals: Outer Side: Red-Purple Group N57B. Inner Side: Red-Purple Group N57A. Innermost petals: Outer Side: Red-Purple Group N57B. Inner Side: Red-Purple Group N57A.

*Upon opening, basal petal spots.*—Basal petal spot, outermost petals: Outer Side: Green-Yellow Group 1C. Inner Side: Green-Yellow Group 1C. Basal petal spot, innermost petals: Outer Side: Green-Yellow Group 1C. Inner Side: Green-Yellow Group 1C.

*After opening, petals.*—Outermost petals: Outer Side: Red-Purple Group N57B. Inner Side: Red-Purple Group N57A. Innermost petals: Outer Side: Red-Purple Group N57B. Inner Side: Red-Purple Group N57A.

*After opening, basal petal spots.*—Basal petal spot, outermost petals: Outer Side: Green-Yellow Group 1C. Inner Side: Green-Yellow Group 1C. Basal petal spot, innermost petals: Outer Side: Green-Yellow Group 1D. Inner Side: Green-Yellow Group 1D. Variegations: None.

General Tonality: On open flower Red-Purple Group N57A. No change in the general tonality at the end of the 8th day. Afterwards, general tonality is Red-Purple Group N57C.

Petals:

*Petal count.*—Approximately 35-40 petals under normal conditions.

*Petal reflex.*—Petals reflex slightly strongly.

*Petal edge.*—Entire.

*Petal shape.*—Round to deltoid. Apex shape is round. Shape of base is acute.

*Petal size.*—18-20 mm long; 20-22 mm wide.

*Thickness.*—Average.

*Petal arrangement.*—Generally in a regular pattern with overlapping edges.

*Petaloids.*—Present.

*Petaloid count.*—Average of 5-10 per flower.

*Petaloid edge.*—Entire.

*Petaloid texture.*—Rugose.

*Petaloid shape.*—Linear to elliptic.

*Petaloid size.*—Petaloids are 8-15 mm long and 7-10 mm wide.

*Petaloid color.*—Color of inner side is Red-Purple Group N57A. Color of outer side is Red-Purple Group N57B with intonations of White N155C.

Reproductive organs:

*Pistils.*—Approximately 30-40 present. Stigmas: Location: Superior in position to anthers. Color: Greyed-Yellow Group 160D. Styles: Length: 4 mm long. Color: Greyed-Yellow Group 160D.

*Stamens.*—Approximately 40-50 on average and regularly arranged. Anthers: Size: 1 mm long. Color: Orange Group 26C. Pollen: Absent. Filaments: Color: Yellow Group 2A. Length: 4-5 mm.

THE PLANT

*Plant growth.*—Moderately vigorous. Upright to bushy habit. When grown as an 8-11 cm pot plant, the average height of the plant itself is 20-25 cm and the average width is 20-22 cm.

*Stems.*—Stem color: Young wood: Yellow-Green Group 144B. Older wood: Green Group 138A. Stem surface: Young wood: Smooth. Older wood: Smooth.

*Prickles.*—Present. Incidence: 2-5 per 10 cm of stem. Size: Average length: 4 mm. Color: Immature prickles: Orange-White Group 159B. Mature prickles: Greyed-Orange Group N167D. Senescing to Greyed-Orange Group N167A. Shape: Deeply concave. Anthocyanin: Absent.

*Leaves and leaflets.*—Normally 3-5 leaflets on normal leaves in middle of the stem. Venation pattern: Pyramidal net pattern. Leaf size: 80-90 mm (l)×45-55 mm (w). Quantity: Abundant. Texture: Upper side of leaflet: Semi glossy. Smooth. Under side of leaflet: Semi glossy. Rough. Color, mature foliage: Upper Leaf Surface: Green Group 138A. Lower Leaf Surface: Green Group 138B. Color, juvenile foliage: Upper Leaf Surface: Yellow-Green Group 144A. Lower Leaf Surface: Green Group 138A. Anthocyanin intonation: Absent.

*Stipules.*—Size: 8-9 mm long. 4 mm between the tips of the stipule. Main body of stipule 2-3 mm in width. Shape: Longitudinally flanged or winged along middle. Stipule color: Yellow-Green Group 144A and Yellow-Green Group 144B. Presence of stipitate glands: Very few on margins. Margins: Few stipitate glands.

*Petiole.*—Length: 10 mm-12 mm. Diameter: 1 mm. Petiole color: Yellow Green Group 144A. Underneath: An occasional prickle underneath. Stipitate glands: Limited numbers of stipitate glands on margins.

*Petiole rachis.*—Length: 15 mm. Diameter: 1 mm. Color: Yellow-Green Group 144A. Prickles: An occasional prickle underneath. Stipitate glands: Limited numbers of stipitate glands on margins.

*Leaflets.*—Size: Average size of the terminal leaflet is 35 mm (l)×20 mm (w). Shape: Ovate. Base: Ovate. Apex: Acute. Surface: Upper side: Semi-glossy. Lower side: Matte. Margins: Finely serrated. Texture: Thin.

Hips/seed formation: None observed. The plant has not been grown to the stage of hip and seed development due to its use as a greenhouse grown flowering potted plant.

Winter hardiness: Due to the variety's principal use in greenhouses, winter hardiness has not been evaluated.

Disease resistance: Very good resistance to powdery mildew (*Sphaerotheca pannosa*) and *Botrytis* (*Botrytis cinerea*) diseases under normal growing conditions.

I claim:

1. A new and distinct variety of miniature rose plant as herein illustrated and described:

(a) Forms abundant, attractive long lasting hot pink flowers;

(b) Exhibits an upright and bushy growth habit;

(c) Is suited for growing in greenhouse in pots from softwood cuttings, and;

(d) Exhibits durable flowers and foliage suitable for distribution in the floral industry;

substantially as herein illustrated and described.

* * * * *

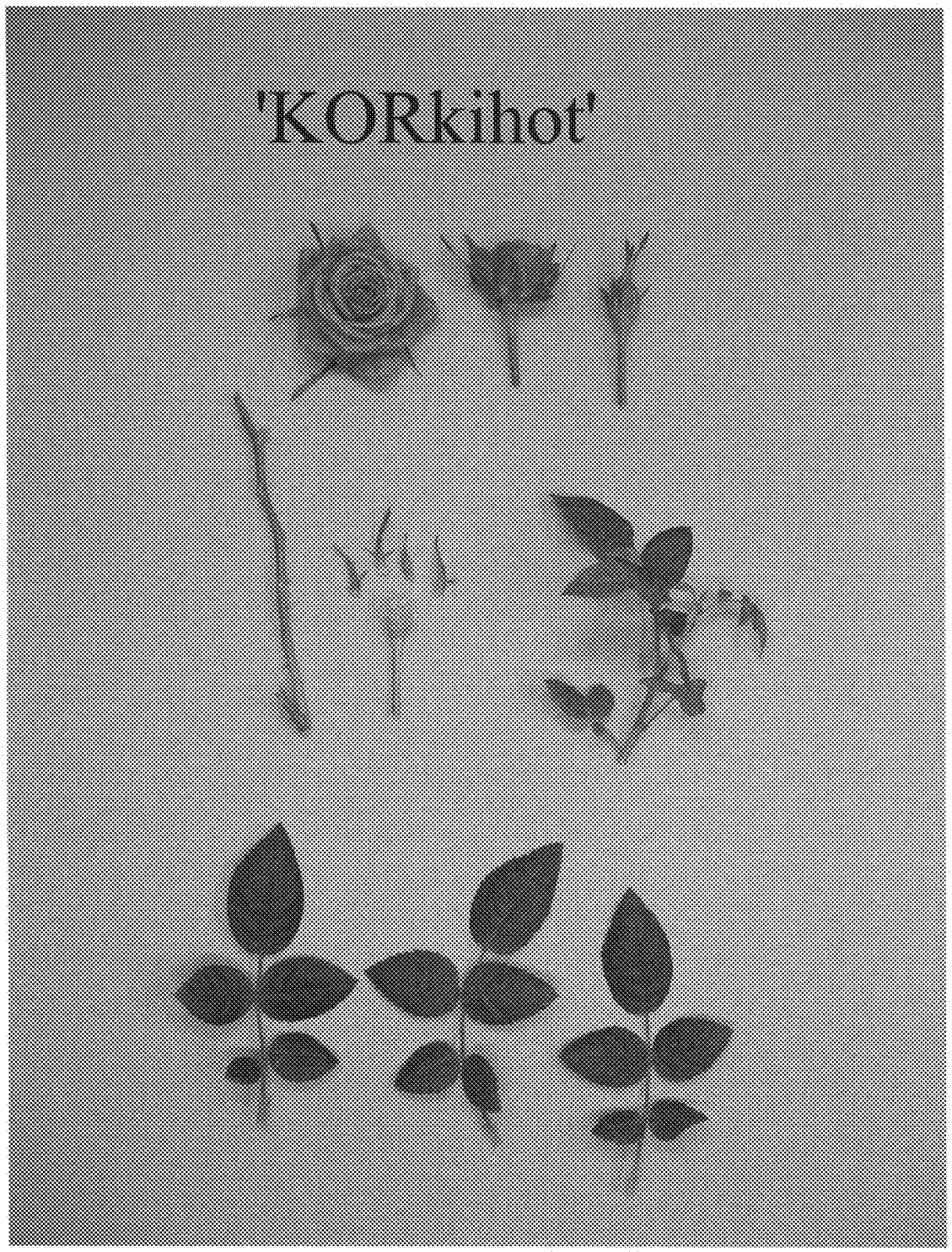
'KORkihot'